(12) United States Patent
Schneidewend et al.

(10) Patent No.: US 7,873,409 B2
(45) Date of Patent: Jan. 18, 2011

(54) INVASIVE CARDIOLOGY DIGITAL SIGNAL AMPLIFIER AND ACQUISITION DEVICE

(75) Inventors: Daniel R. Schneidewend, Menomonee Falls, WI (US); James M. Peschke, Harvard, IL (US); Michael McOlash, Wauwatosa, WI (US); Rodger F. Schmit, West Bend, WI (US)

(73) Assignee: General Electric Company, Schenectady, NY (US)

( * ) Notice: Subject to any disclaimer, the term of this patent is extended or adjusted under 35 U.S.C. 154(b) by 426 days.

(21) Appl. No.: 11/467,372

(22) Filed: Aug. 25, 2006

(65) Prior Publication Data
US 2007/0276272 A1 Nov. 29, 2007

Related U.S. Application Data

(60) Provisional application No. 60/800,370, filed on May 15, 2006.

(51) Int. Cl.
*A61B 5/02* (2006.01)
(52) U.S. Cl. ........................................ 600/509; 600/301
(58) Field of Classification Search .................. 600/509, 600/301
See application file for complete search history.

(56) References Cited

U.S. PATENT DOCUMENTS

| 5,368,565 A | * | 11/1994 | DeLong | 604/100.03 |
| 6,183,417 B1 | * | 2/2001 | Geheb et al. | 600/301 |
| 6,544,173 B2 | * | 4/2003 | West et al. | 600/300 |

* cited by examiner

*Primary Examiner*—Eric D. Bertram
(74) *Attorney, Agent, or Firm*—Andrus, Sceales, Starke & Sawall, LLP

(57) ABSTRACT

The digital signal amplifier and acquisition system includes at least one catheter input module (CIM) configured to receive, route and digitize incoming analog cardiac signals from a number of catheters, as well as outgoing stimulator pulses. A plurality of CIMs are mechanically stacked and electrically daisy-chained and coupled with a mounting. The mounting platter is clamped to the bedrail and provides a single digital output cable to the base. The system also includes an acquisition device and the aforementioned base, which is configured to collect, filter and distribute the acquired data. Lastly an analog output module receives filtered digital signals from the base and is configured to reconstruct analog representations of such filtered digital signals for outside devices.

12 Claims, 3 Drawing Sheets

US 7,873,409 B2

INVASIVE CARDIOLOGY DIGITAL SIGNAL AMPLIFIER AND ACQUISITION DEVICE

RELATED APPLICATIONS

The present application is based on and claims priority to U.S. Provisional Patent Application Ser. No. 60/800,370, filed May 15, 2006.

FIELD OF THE INVENTION

The subject matter described herein generally relates to the field of invasive cardiology, and more particularly, the invention relates to the field of digital signal amplification and acquisition systems.

BACKGROUND OF THE INVENTION

In order to properly and accurately diagnose cardiac conditions, it is important for the physician to have clear and clean cardiograms at his or her disposal. Therefore, an acquisition system for cardiac behavior must capture electrophysiological signals accurately as small as 6 uV. These signals must be captured with very little noise, and displayed, stored and sent to other medical equipment in a real-time manner.

These electrophysiological signals must be filtered in a number of ways and the captured data within the signals must reject artifacts caused by other equipment, such as pacemaker or ablation devices. Current systems offer various trade-offs in terms of speed, noise and resolution. In other words, the additional cabling in all current systems acts as an antenna for stray electromagnetic signals, and as a result, constitutes a primary noise source in those systems. Many current systems have 16 or less bits of A/D resolution and sample at typical low ranges of 1 to 2 KHz. Furthermore, current systems do not typically embody a quick real-time response for data capture and display, nor do they include complete modularity.

BRIEF DESCRIPTION OF THE INVENTION

The digital signal amplifier and acquisition system includes at least one catheter input module (CIM) configured to receive, route and digitize incoming analog cardiac signals from a number of catheters, as well as outgoing stimulator pulses. A plurality of CIMs are mechanically stacked and electrically daisy-chained and coupled with a mounting platter. The mounting platter is clamped to the bedrail and provides a single digital cable to the base. The system also includes an acquisition device and the aforementioned base, which is configured to collect, filter and distribute the acquired data. Lastly an analog output module receives filtered digital signals from the base and is configured to reconstruct analog representations of such filtered digital signals for outside devices.

In one embodiment, an invasive cardiology digital signal amplifier and acquisition system is provided. The system includes at least one catheter input module, the at least one catheter input module configured to receive a set of analog cardiac data from a patient catheter, the at least one catheter input module including a digitizer configured to convert the set of analog cardiac data to a set of digital data, a mount platter mechanically and electrically coupled to the at least one catheter input module, the mount platter configured to receive the set of digital data from the at least one catheter, and a base unit coupled with the mount platter with a digital cable, the base unit configured to receive the set of digital data, and further configured to filter and distribute the set of digital data. The system further comprises an analog output module coupled with the base unit and configured to receive a filtered set of digital data from the base unit, and further configured to convert the filtered set of digital data to a reconstructed analog signal, an acquisition device coupled with the base unit, the acquisition device configured to control the collection of a plurality of physiological parameters from a patient and wherein the mount platter includes an emergency stimulator connector configured to provide a pulse to the patient catheter even in the event of total system failure, which may include an auxiliary reference input configured to collect a non-catheter patient input. The system further wherein the at least one catheter input module includes a plurality of inputs, the mount platter includes a test signal generator configured to test the functionality of any of the plurality of inputs of the catheter input module and wherein each of the plurality of catheter input modules is electrically and mechanically coupled to each other and with the mount table wherein the mount platter is fastened to a patient bed.

In another embodiment, a method of cardiology signal acquisition and amplification is provided. The method comprises the steps of collecting a set of analog cardiac data from a patient catheter, converting the set of analog cardiac data to a set of digital data with a cardiac input module, the cardiac input module including an analog to digital converter, collecting the set of digital data with a mount platter, transmitting the set of digital data to a base unit, wherein the base unit is configured to filter and distribute the set of digital data and comprises receiving a filtered set of digital data in an analog output module from the base unit, wherein the analog output module is configured to convert the filtered set of digital data to a reconstructed analog signal. The method further comprises coupling an acquisition device coupled with the base unit, the acquisition device configured to control the collection of a plurality of physiological parameters from a patient wherein the mount platter includes an emergency stimulator connector configured to provide a pulse to the patient catheter even in the event of total system failure the mount platter including a auxiliary reference input configured to collect a non-catheter patient input wherein the at least one catheter input module includes a plurality of inputs, and further wherein the mount platter includes a test signal generator configured to test the functionality of any of the plurality of inputs of the catheter input module, and wherein at least one catheter input module is a plurality of catheter input modules, wherein each of the plurality of catheter input modules is electrically and mechanically coupled to each other and with the mount table wherein the mount platter is fastened to a patient bed.

DETAILED DESCRIPTION

The digital signal amplifier and acquisition system relocates the cardiac signal digitization from a point many feet away from the patient, up to the patient's bedside, thereby eliminating a significant amount of noise induced by analog cabling. It has been found that analog cabling causes approximately half of the noise found in current acquisition systems, and current systems include catheter input modules (CIMs) that do not include digitizers, but rather act only as inputs with analog cables that connect to the digitizer, typically in the base several feet away, or attached to the underside of the bed. The present digital signal amplifier and acquisition system also directly converts the analog signal to a digital signal without amplifying the analog signal or applying any band pass filtering, which also reduces a significant amount of signal noise.

Figure 1:
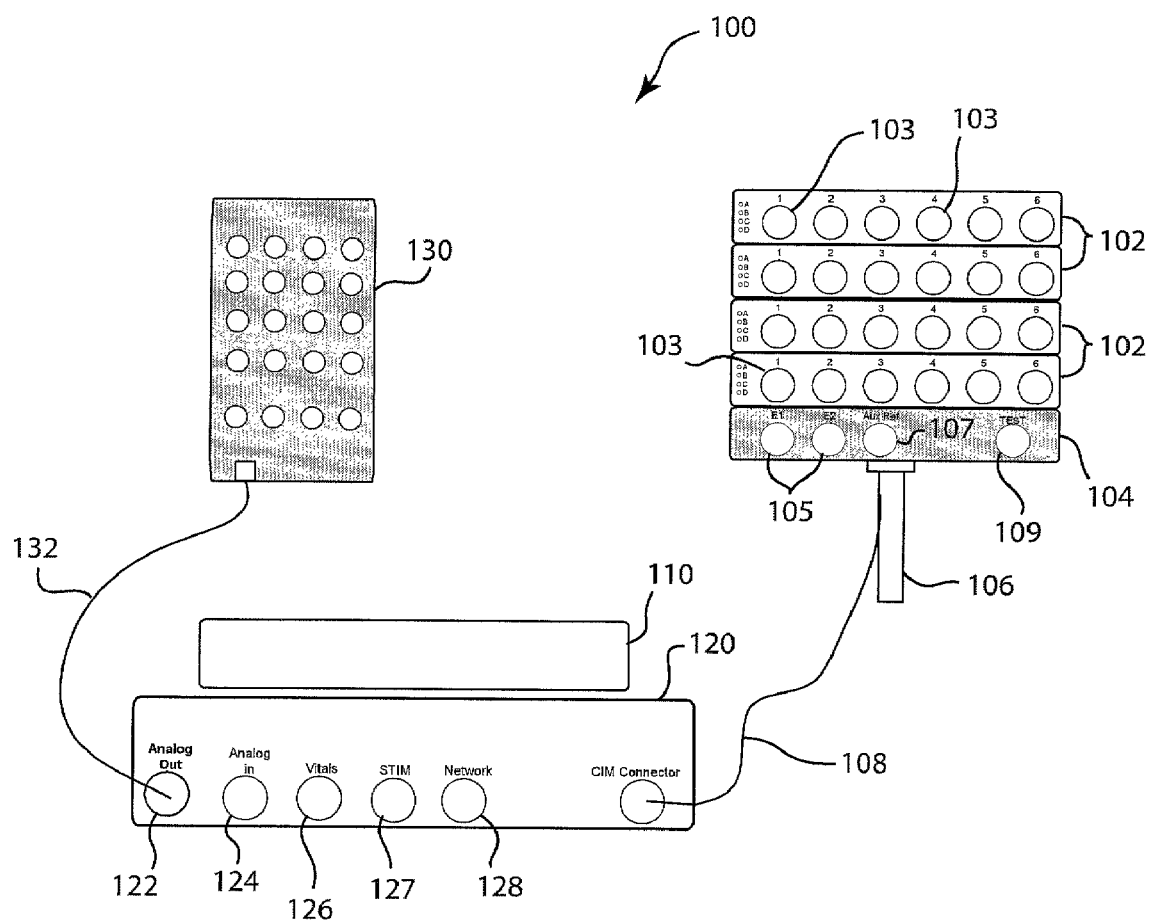
FIG. 1 illustrates an embodiment of a block diagram of a method of signal acquisition and amplification.

FIG. 1 shows an embodiment of the acquisition system 100 that includes one or more catheter input modules (CIM) 102 which have a technical effect to receive incoming cardiac signals from a catheter, and route and digitize those signals. The system 100 will be able to accommodate four such CIMs, each with 30 channels for a total of 120 channels. The catheters (not shown) will connect via the 6, 10-pin connectors 103, in each of the CIMs 102. As illustrated in FIG. 1, all of the CIMs 102 are manually stacked and electrically daisy-chained (FIG. 2) via a short cable on the rear of the CIM 102, and held on the patient's bedside with a mount platter 104. The CIM 102 is a 4 KHz 24-bit sigma delta A/D digitizer, bipolar or unipolar with respect to a Wilson central terminal or auxiliary reference, respectively.

Still referring to FIG. 1, the mount platter 104 is configured to hold and support the CIMs 102, and provide emergency and reference input sources 105, 107, 109. The mount platter 104 utilizes an attachment pole 106 in order to clamp the mount platter 104 to the bedrail of the patient's bed. The mount platter 104 also includes a single CIM cable 108, which provides digital signals from the CIMs 102 to the base 120. The mount platter 104 also includes emergency stimulator connectors 105, as well as an auxiliary reference input 107 and a test signal generator 109. The emergency stimulator connectors 105 provide the ability to utilize the catheters placed in the patient as emergency pacemakers in the event of total failure of the system 100. The emergency stimulator connectors 105 provide for a direct electrical connection to the STIM inputs number 1 and 2 provided on the STIM connector 127 on the base unit 120. The auxiliary reference input 107 allows a physician to build an analog channel without using a catheter and the CIMs 102. In other words, a physician may utilize a device such as a patch on the back of the patient or an electrode in the leg of the patient and plug this device into the auxiliary reference input 107 to provide an additional input. The test input 109 allows a test of any of the CIMs 102 by plugging a connector from the test input 109 into any of the ten pin connectors 103 in any of the CIMs 102 in order to see if the CIM 102 is working properly.

Figure 2:
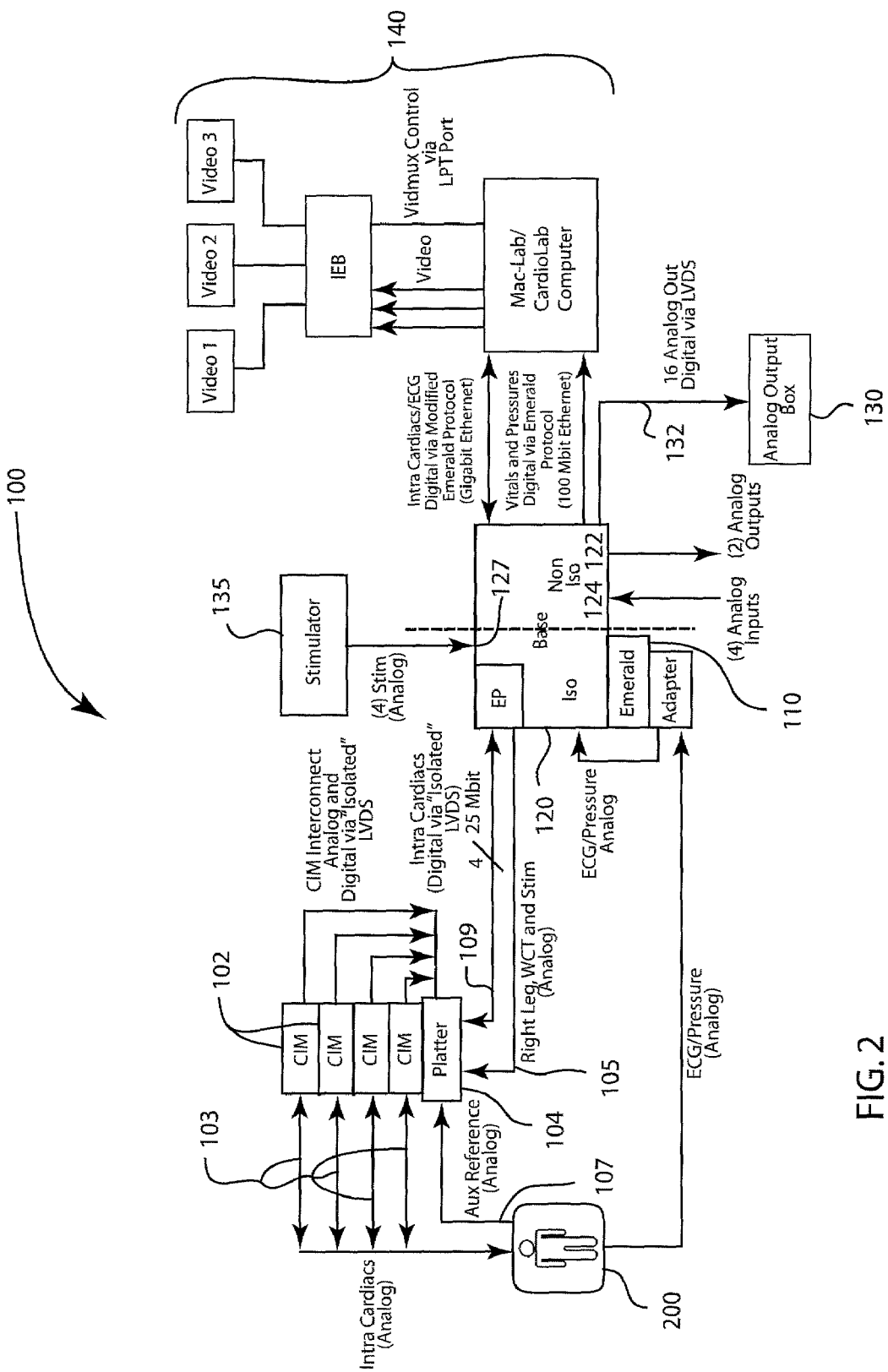
FIG. 2 illustrates a schematic diagram of an embodiment of digital amplifier and acquisition system.
Figure 3:
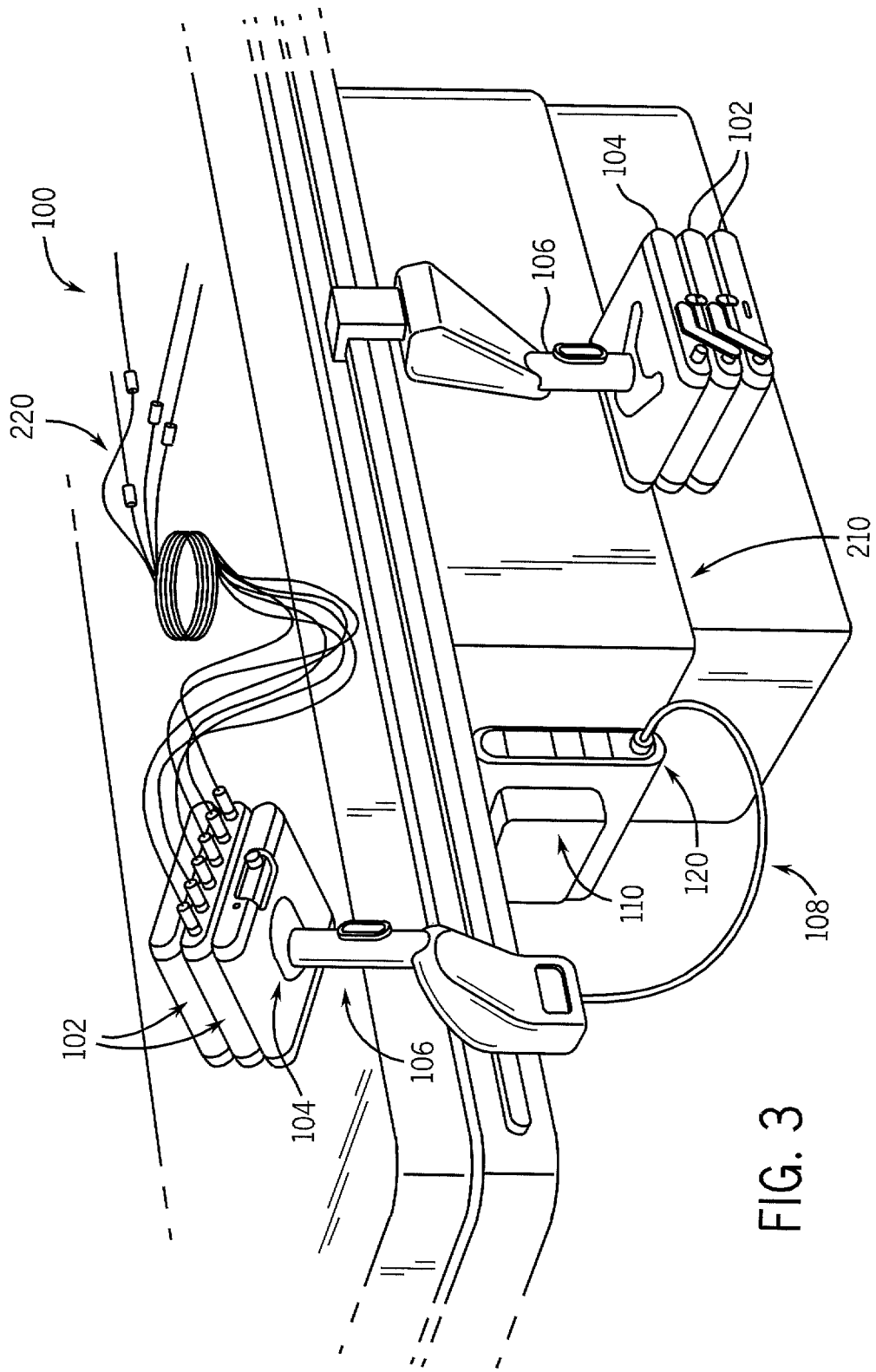
FIG. 3 illustrates a graphical representation of another embodiment of the system of a digital amplifier and acquisition system.

Referring now to FIGS. 1 and 2 the system 100 also includes an acquisition module 110 and a base 120. The base 120 is configured to receive the digital signals from the mount platter 104 through the CIM cable 108 and filters and distributes this acquired data. The base 120 is also configured to give a digital command to the CIMs 102 in order to instruct the CIMs 102 when to digitize the information, and is further configured to package the digital data from the CIMs 102 in order to send it to a PC or outside device for additional processing. The base 120 is preferably mounted on the base of the patient's bed 210 (FIG. 3). The acquisition device 110 is mechanically and electrically coupled with the base, and is configured to collect a number of physiological parameters from the patient such as blood pressure, heart rate, respiratory data, and blood oxygen saturation level. The base 120 includes 8 bipolar simulator inputs which are digitized and routed, 4 analog inputs, which are digitized in synchronous with CIM sampling, 12 lead ECG and 4 IBP analog signals shared with the acquisition module 110, and 16 low-latency analog outputs.

Referring back to FIG. 1, the base 120 includes an analog out 122, which provides a digital signal through the cable 132 to the analog output module 130. The base 120 also includes an analog input 124, a vital sign output 126, a simulator input 127 and a network connection 128. Referring again to FIG. 2, the stimulator input 127 receives inputs from the stimulator 135, while the outside devices 140 send request and receive processed and filtered data from the base 120 for physician review.

The system 100 also includes an analog output module 130. The analog output module 130 is configured to receive a digital signal from the analog out 122 of the base 120 through the cable 132, and reconstruct an analog signal, preferably with up to 16 filtered digital data streams at a time. The analog output module 130 is configured to reconstruct the analog signal for a strip chart recorder, or any other outside device that requires a representation of the signal.

Referring now to FIG. 3, a graphical representation of an embodiment of the system 100 of the present invention is depicted. Here, the catheters 220 are connected into the CIMs 102, which are mechanically stacked and daisy-chained to the mount platter 104. The attachment pole 106 allows the mount platter 104 to be attached to the bedrail of the patient's bed 210, and a single CIM cable 108 allows digital signals to be communicated from the mount platter 104 to and from the base 120. As is shown, the base 120 is mounted on the patient bed 210 and an acquisition device 110 is coupled with the base 120.

The system 100 reduces a large amount of system noise by digitizing the analog signals at a close proximity to the patient, eliminating many feet of analog cable from the systems of the prior art. Furthermore, a large amount of system noise is removed by eliminating analog switching and filtering circuits, which is done by performing all signal processing after the CIMs in the digital domain.

Furthermore, an embodiment utilizes a 4 KHz, 24-bit A/D converter which provides greater than 20 bits of signal resolution when noise is accounted for. This large number of bits provides the system 100 the ability to record signals down to the physiological minimal level of interest of 6 uV over an input range of almost 5 volts. A range and resolution this large allows for recording all data of interest even in non-ideal conditions such as pacemaking or ablating. In other words, the system 100 has a much higher resolution and range than conventional systems.

The system 100 of the present invention also embodies a real-time response. It is important that data be captured and displayed or sent to other equipment as quickly as possible in such systems. The digital base 120 of the system 100 includes a high-speed processor and programmable logic able to receive over 150 channels of data at 24 bits and 4 KHz. Preferably, the data is placed in Ethernet frames and sent at 250 Hz at the same time it is filtered and sent out in analog form in less than 2 mS.

Furthermore, the system 100 of the present invention is versatile from a market standpoint, as it incorporates a set of modular CIMs 102. Preferably, each CIM 102 accepts 60 inputs, captures 30 unipolar or bipolar channels, and the system 100 is configured to support from 1 to 4 CIMs 102. Additionally, two analog outputs are provided on the base 120, and with additional analog output module support, such analog outputs are expanded to 16 outputs.

Subject matter has been described in terms of specific embodiments incorporating details to facilitate the understanding of the principals of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A data acquisition system in communication to receive a set of analog cardiac data from a catheter of a patient situated on a support structure, the system comprising:
    at least one catheter input module configured to receive the set of analog data from a patient and to convert the set of analog cardiac data to a set of digital data, wherein the catheter input module includes a plurality of connectors configured to receive analog data, and further wherein the catheter input module is configured to be physically and electrically coupled with additional catheter input modules;
    a mount platter removably coupled to a patient bed in close proximity to the patient, and further coupled in communication to receive the set of digital data from the at least one catheter input module, wherein the mount platter is removably coupled to the at least one catheter input module and supporting the at least one catheter input module; and
    a base unit coupled in communication to receive the set of digital data from the mount platter and further configured to filter and distribute the set of digital data, wherein the base unit is physically coupled to the patient bed, wherein the mount platter includes an emergency stimulator connector coupled with a STIM input and configured to provide a pulse to the catheter from the STIM input, wherein the pulse from the emergency stimulator connector is provided in the event of total system failure.

2. The system as claimed in claim 1, further comprising an analog output module electrically coupled with the base unit and configured to receive a filtered set of digital data from the base unit, and further configured to convert the filtered set of digital data to a reconstructed analog signal.

3. The system as claimed in claim 1, further comprising an acquisition device coupled with the base unit, the acquisition device configured to control the collection of a plurality of physiological parameters from a patient.

4. The system as claimed in claim 1, wherein the mount platter includes an auxiliary reference input configured to collect a non-catheter patient input.

5. The system as claimed in claim 1, wherein the at least one catheter input module includes a plurality of inputs.

6. The system as claimed in claim 5, wherein the mount platter includes a test signal generator configured to test the functionality of any of the plurality of inputs of the catheter input module.

7. The system as claimed in claim 5, further comprising a plurality of catheter input modules, wherein each of the plurality of catheter input modules is electrically and mechanically coupled to each other and with the mount platter.

8. A data acquisition system in communication to receive a set of analog cardiac data from a catheter of a patient situated on a support structure, the system comprising:
    at least one catheter input module configured to receive the set of analog data from a patient and to convert the set of analog cardiac data to a set of digital data, wherein the catheter input module includes a plurality of connectors configured to receive analog data, and further wherein the catheter input module is configured to be physically and electrically coupled with additional catheter input modules;
    a mount platter removably coupled to a patient bed in close proximity to the patient, and further coupled in communication to receive the set of digital data from the at least one catheter input module, wherein the mount platter is removably coupled to the at least one catheter input module and supporting the at least one catheter input module; and
    a base unit coupled in communication to receive the set of digital data from the mount platter and further configured to filter and distribute the set of digital data, wherein the base unit is physically coupled to the patient bed, wherein the at least one catheter input module includes a plurality of inputs, and further wherein the mount platter includes a test signal generator configured to test the functionality of any of the plurality of inputs of the catheter input module.

9. The system as claimed in claim 8, further comprising an analog output module electrically coupled with the base unit and configured to receive a filtered set of digital data from the base unit, and further configured to convert the filtered set of digital data to a reconstructed analog signal.

10. The system as claimed in claim 8, further comprising an acquisition device coupled with the base unit, the acquisition device configured to control the collection of a plurality of physiological parameters from a patient.

11. The system as claimed in claim 8, wherein the mount platter includes an auxiliary reference input configured to collect a non-catheter patient input.

12. The system as claimed in claim 8, further comprising a plurality of catheter input modules, wherein each of the plurality of catheter input modules is electrically and mechanically coupled to each other and with the mount platter.

* * * * *